(12) United States Patent
Jaberi et al.

(10) Patent No.: US 10,813,305 B2
(45) Date of Patent: Oct. 27, 2020

(54) REGENERATION AND TRANSFORMATION OF COSMOS BIPINNATUS PLANTLETS

(71) Applicants: Mahdi Jaberi, Karaj (IR); Pejman Azadi, Karaj (IR)

(72) Inventors: Mahdi Jaberi, Karaj (IR); Pejman Azadi, Karaj (IR)

(*) Notice: Subject to any disclaimer, the term of this patent is extended or adjusted under 35 U.S.C. 154(b) by 230 days.

(21) Appl. No.: 15/369,825

(22) Filed: Dec. 5, 2016

(65) Prior Publication Data

US 2017/0231177 A1 Aug. 17, 2017

Related U.S. Application Data

(60) Provisional application No. 62/265,549, filed on Dec. 10, 2015.

(51) Int. Cl.
  *A01H 4/00* (2006.01)
  *C12N 15/82* (2006.01)

(52) U.S. Cl.
  CPC .............. *A01H 4/008* (2013.01); *A01H 4/005* (2013.01); *C12N 15/8205* (2013.01)

(58) Field of Classification Search
  None
  See application file for complete search history.

(56) References Cited

U.S. PATENT DOCUMENTS

| 4,548,901 A | 10/1985 | Christianson et al. |
| 4,855,236 A | 8/1989 | Levin |
| 5,262,316 A * | 11/1993 | Engler ............... C12N 15/8205 800/294 |
| 5,898,001 A | 4/1999 | Kumar et al. |
| 5,969,215 A | 10/1999 | Hall et al. |
| 6,197,587 B1 | 3/2001 | Guiltinan et al. |
| 2005/0066393 A1* | 3/2005 | Takano ............... C12N 15/827 800/286 |
| 2013/0055472 A1 | 2/2013 | Cho et al. |

OTHER PUBLICATIONS

Jang et al. (Plant Foods Hum Nutr (2008) 63:205-210). (Year: 2008).*
Bhatia et al. (In Vitro Cellular & Developmental Biology-Plant 41.4 (2005): 457-464). (Year: 2005).*
A. Sharafi, Tissue culture and regeneration of an antimalarial plant, Artemisia sieberi Besser, Research Journal of Pharmacognosy, Apr. 2014, vol. 1, Issue 3, pp. 15-20.

* cited by examiner

*Primary Examiner* — Charles Logsdon
(74) *Attorney, Agent, or Firm* — Bajwa IP Law Firm; Haris Zaheer Bajwa

(57) ABSTRACT

*Cosmos bipinnatus* cotyledons are isolated as explants, and the isolated explants are cultured onto a regeneration medium to obtain regenerated *Cosmos bipinnatus* shoots. The regeneration medium optionally includes a basal medium, a cytokinin, an ethylene action inhibitor, and a nitrogen source.

13 Claims, 14 Drawing Sheets

REGENERATION AND TRANSFORMATION OF COSMOS BIPINNATUS PLANTLETS

CROSS REFERENCE TO RELATED APPLICATION

This application claims the benefit of priority from U.S. Provisional Patent Application Ser. No. 62/265,549, filed on Dec. 10, 2015, and entitled "A PROTOCOL FOR ORGANOGENESIS AND *AGROBACTERIUM TUMEFACIENS* MEDIATED-TRANSFORMATION IN *COSMOS BIPINNATUS*," which is incorporated by reference herein in its entirety.

TECHNICAL FIELD

The present application generally relates to the field of plant biotechnology, specifically to a protocol for regeneration of *Cosmos bipinnatus* plantlets, and more specifically to a protocol for regeneration and transformation of *Cosmos bipinnatus* plantlets.

BACKGROUND

*Cosmos bipinnatus*, which belongs to the Asteraceae family, is an annual plant that is native to Mexico and Southern America. There are about 25 species in the *Cosmos* genus. *Cosmos bipinnatus* is the most common species that is highly sought, due to its ornamental and medicinal value and uses. The *Cosmos bipinnatus* flowers are edible. The flowers are about 5-10 cm in diameter, and come in various colors, such as red, purple, yellow and white. These edible flowers have been used in traditional medicine to treat jaundice, intermittent fever, and splenomegaly. The extract of *Cosmos* flower has strong antioxidant and antigen toxin activity, thereby protecting DNA from oxidative damage. The antimalarial activity of the extract has also been reported in the art. Therefore, *Cosmos bipinnatus* may be considered a very convenient species for genetic manipulation for the purpose of creating new varieties with different flower colors and secondary metabolite production.

An efficient plant regeneration protocol can facilitate the establishment of genetic transformation. Genetic engineering via *agrobacterium*-mediated transformation can be used, for example, to improve disease resistance and modify flower color in plants.

There is therefore a need in the art for a successful regeneration and *Agrobacterium tumefaciens*-mediated transformation protocol in the *Cosmos bipinnatus* to facilitate genetic transformation projects, such as changing the color of the flower and producing secondary metabolites in *Cosmos bipinnatus*.

SUMMARY

The following brief summary is not intended to include all features and aspects of the present application, nor does it imply that the application must include all features and aspects discussed in this summary.

In one general aspect, the present disclosure describes a method for *Cosmos bipinnatus* plant regeneration. Steps in the method may include: isolating *Cosmos bipinnatus* cotyledons as explants, and then culturing the explants in a regeneration medium to obtain regenerated *Cosmos bipinnatus* shoots. The regeneration medium may include a basal medium, a cytokinin, an ethylene action inhibitor, and a nitrogen source.

Methods according to the above-described general aspect may include one or more further features. Examples of such further features can include: step of culturing the regenerated shoots onto an elongation medium to obtain elongated shoots; and step of culturing the elongated shoots onto a rooting medium to obtain rooted *Cosmos bipinnatus* plantlets.

According to some implementations, the basal medium may be a Murashige and Skoog (MS) medium. The cytokinin may be selected from benzyladenine (BA), Thidiazuron (TDZ), or combinations thereof. According to an implementation, the cytokinin may have a concentration in a range of about 2 mg/l to about 5 mg/l.

According to an implementation, the ethylene action inhibitor may have a concentration in a range, for example, of about 2 mg/l to about 5 mg/l. According to another implementation, the ethylene action inhibitor may be silver nitrate with a concentration in a range, for example, of about 2 mg/l to about 5 mg/l.

According to other implementations, the nitrogen source inhibitor may have a concentration in a range, for example, of about 10 mg/l to about 40 mg/l. According to an implementation, the nitrogen source may be selected from, for example, adenine sulfate, glutamine sulfate, or combinations thereof.

According to some implementations, isolating the *Cosmos bipinnatus* cotyledon may include steps of: sterilizing *Cosmos bipinnatus* seeds; germinating sterilized *Cosmos bipinnatus* seeds to obtain cotyledons of *Cosmos bipinnatus* plant; and cutting the cotyledons from the *Cosmos bipinnatus* plant and using them as explants.

In another general aspect, the present disclosure describes a method for *Cosmos bipinnatus* plant transformation and regeneration. Steps in the method may include: isolating *Cosmos bipinnatus* cotyledons as explants; preparing *Agrobacterium tumefaciens* as an Agrobacteria suspension; inoculating the explants with the prepared *Agrobacterium Tumefaciens*; co-culturing the inoculated explants with *Agrobacterium tumefaciens* in a co-cultivation medium to obtain transformed explants; and culturing the transformed explants in a regeneration medium to obtain regenerated transformed shoots. The regeneration medium includes a basal medium, a cytokinin, an ethylene action inhibitor, a nitrogen source, and antibiotics for eliminating the *Agrobacterium*.

Methods for *Cosmos bipinnatus* plant regeneration according to the above-described general aspect may include one or more additional features. Example additional features can include: step of culturing the regenerated transformed shoots onto an elongation medium to obtain elongated transformed shoots; and step of culturing the elongated transformed shoots onto a rooting medium to obtain rooted transformed *Cosmos bipinnatus* plantlets.

According to an implementation, preparing *Agrobacterium tumefaciens* may include: culturing *Agrobacterium tumefaciens* in a Lysogeny broth (LB) containing selective antibiotics; and inoculating the *Agrobacterium tumefaciens* in an inoculation medium to obtain an Agrobacteria suspension.

According to some implementations, antibiotics for eliminating the *Agrobacterium* may include Cefotaxime. According to another implementation, the antibiotics for eliminating the *Agrobacterium* are present in the regeneration medium with a concentration of about 200 to about 300 mg/l.

BRIEF DESCRIPTION OF THE DRAWINGS

While the specification concludes with claims particularly pointing out and distinctly claiming the subject matter that is regarded as forming the present application, it is believed that the application will be better understood from the following description taken in conjunction with the accompanying DRAWINGS, where like reference numerals designate like structural and other elements, in which:

DETAILED DESCRIPTION

Disclosed herein is a method for regenerating *Cosmos bipinnatus* plants that involves isolating *Cosmos bipinnatus* cotyledons as explants and culturing the explants in a regeneration medium to obtain regenerated *Cosmos bipinnatus* plantlets. The method, according to one or more aspects of the present disclosure, can provide for transforming *Cosmos bipinnatus* plants to express exogenous DNA, using a transformation protocol, for example, an *Agrobacterium tumefaciens* mediated-transformation protocol.

Figure 1A:
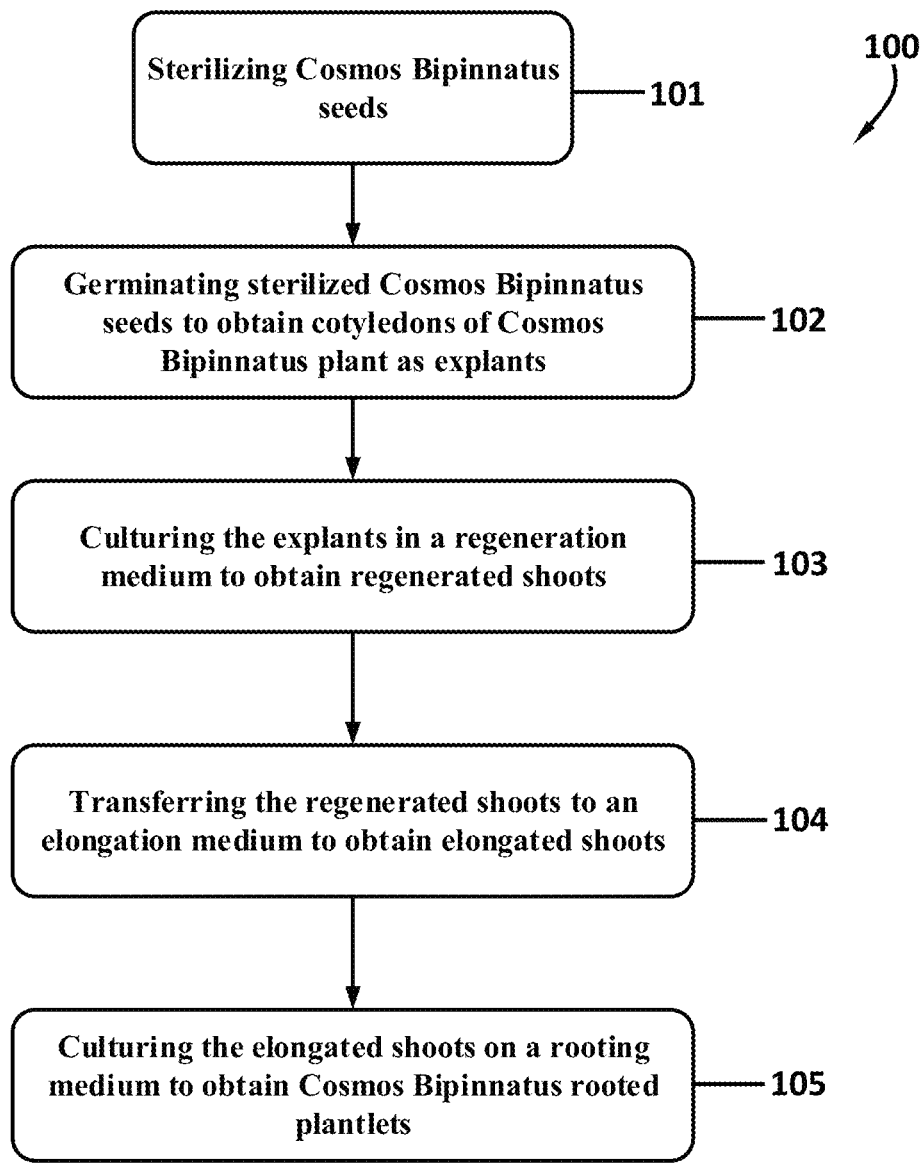
FIG. 1A is a flowchart of example steps in one method for regenerating *Cosmos bipinnatus* plants, according to one or more aspects of the present disclosure.

FIG. 1A is a flowchart of example steps in a method 100 for regenerating *Cosmos bipinnatus* plants. Example steps in the method 100 may include: sterilizing *Cosmos bipinnatus* seeds (step 101); germinating sterilized *Cosmos bipinnatus* seeds to obtain cotyledons of *Cosmos bipinnatus* plant as explants (step 102); and culturing the explants in a regeneration medium to obtain regenerated shoots (step 103). In an aspect, steps in the method 100 may further include: transferring the regenerated shoots to an elongation medium to obtain elongated shoots (step 104); and culturing the elongated shoots on a rooting medium to obtain *Cosmos bipinnatus* rooted plantlets (step 105).

Referring to FIG. 1A, the sterilizing step 101 may involve soaking *Cosmos bipinnatus* seeds in sterilizing solutions, such as ethanol and hypochlorite sodium, and then rinsing the seeds with sterile distilled water to obtain sterilized seeds.

In an implementation, the *Cosmos bipinnatus* seeds may be soaked in an ethanol solution with a concentration of, for example, about 70% volume/volume for about 1 min, followed by soaking the seeds in, for example, a hypochlorite sodium solution with a concentration of about 2% weight/volume for about 10 min. The seeds may be rinsed, for example, three times with sterile distilled water.

Moving on to the next step 102, the sterilized seeds may be transferred, for example, on an agar-solidified Murashige and Skoog (MS) medium under sterile conditions, and may be incubated in a growth chamber with predetermined photoperiods under fluorescent illuminations for the seeds to grow and put out shoots (i.e., germinate). The cotyledons of *Cosmos bipinnatus* plant that grow from germinated seeds may be cut (i.e., provided) as explants. According to an implementation, the temperature of the growth chamber can be in a range, for example, of about 20 to about 25° C. In another implementation, the predetermined photoperiods may be, for example, 16 hours in light and 8 hours in dark. According to another implementation, the seeds may be incubated in the growth chamber for a period of, for example, three days.

Moving on to the next step 103, the explants obtained in step 102 may be cultured in a regeneration medium to obtain regenerated *Cosmos bipinnatus* shoots. In an aspect, the regeneration medium may include a basal medium that may include, for example, a cytokinin, an ethylene action inhibitor, and a nitrogen source.

According to some implementations, the basal medium may be, for example, an MS medium. The cytokinin may be, for example, benzyladenine (BA) or Thidiazuron (TDZ) with a concentration in a range of, for example, about 2 to about 5 mg/l. The ethylene action inhibitor may be, for example, silver nitrate ($AgNO_3$) with a concentration of, for example, about 2 to about 5 mg/l. The nitrogen source may be, for example, adenine sulfate or glutamine sulfate, with a concentration of, for example, about 10 to about 40 mg/l.

According to step 104, the regenerated *Cosmos bipinnatus* shoots may be transferred to an elongation medium to obtain elongated *Cosmos bipinnatus* shoots. According to an implementation, the elongation medium may contain, for example, an MS medium and a cytokinin. The cytokinin may be, for example, BA with a concentration in a range of about 0.5 to about 3 mg/l.

Moving on to step 105, the elongated *Cosmos bipinnatus* shoots may be cultured on a rooting medium to obtain *Cosmos bipinnatus* rooted plantlets. In an implementation, the rooting medium may contain an MS medium supplemented with, for example, about 0.05 to about 3 mg/l Indole-3-butyric acid (IBA). Once *Cosmos bipinnatus* rooted plantlets are obtained they may either be transferred to a plant growth medium or be planted in a pot for further growth and flowering.

Figure 1B:
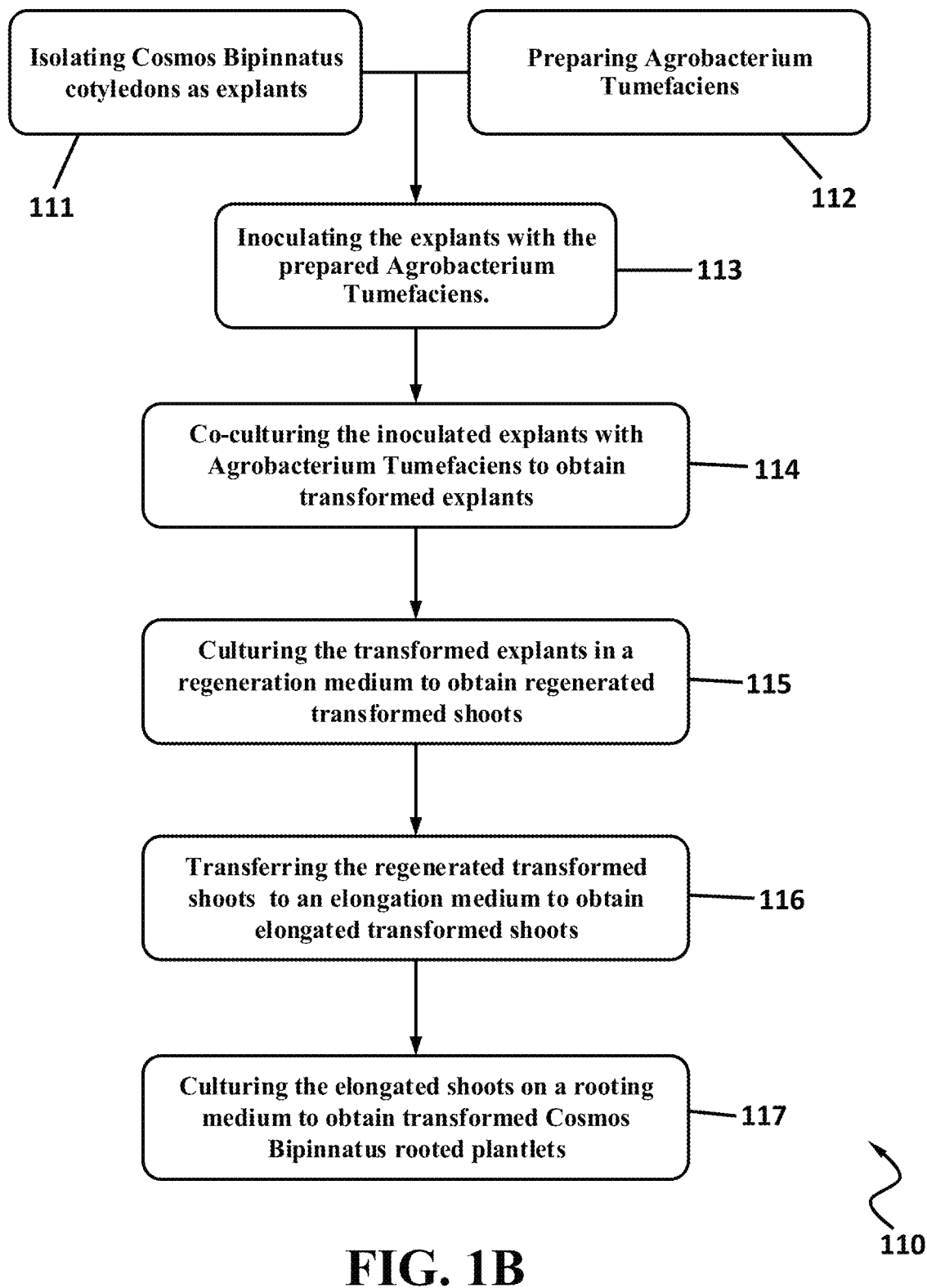
FIG. 1B is a flowchart of example steps in one method for transforming and regenerating transformed *Cosmos bipinnatus* plants, according to one or more aspects of the present disclosure.

FIG. 1B is a flowchart of example steps in a method 110 for transforming and regenerating transformed *Cosmos bipinnatus* plants. Steps in the method 110 may include: isolating *Cosmos bipinnatus* cotyledons as explants (step 111); preparing *Agrobacterium tumefaciens* (step 112); inoculating the explants with the prepared *Agrobacterium tumefaciens* (step 113); co-culturing the inoculated explants with *Agrobacterium tumefaciens* to obtain transformed explants (step 114); and culturing the transformed explants in a regeneration medium to obtain regenerated transformed shoots (step 115). In some aspects, steps in the method 110 may further include: transferring the regenerated transformed shoots to an elongation medium to obtain elongated transformed shoots (step 116); and culturing the elongated transformed shoots on a rooting medium to obtain transformed *Cosmos bipinnatus* rooted plantlets (step 117).

Referring to step 111, in order to isolate *Cosmos bipinnatus* cotyledons as explants, *Cosmos bipinnatus* seeds may be sterilized, then sterilized *Cosmos bipinnatus* seeds may be germinated to obtain cotyledons of *Cosmos bipinnatus* plant, and finally cotyledons of *Cosmos bipinnatus* plant may be cut and isolated as explants.

According to some implementations, *Cosmos bipinnatus* seeds may be soaked in sterilizing solutions, such as ethanol and hypochlorite sodium, and then the seeds may be rinsed with sterile distilled water to obtain sterilized seeds. In an implementation, the *Cosmos bipinnatus* seeds may be soaked in an ethanol solution with a concentration of, for example, about 70% volume/volume for about 1 min. followed by soaking the seeds in, for example, a hypochlorite sodium solution with a concentration of about 2% weight/volume for about 10 min. The seeds may then be rinsed, for example, three times with sterile distilled water.

According to an implementation, the sterilized seeds may be transferred on an agar-solidified MS medium under sterile conditions, and they may be incubated in a growth chamber with predetermined photoperiods under fluorescent illuminations for the seeds to grow into a *Cosmos bipinnatus* plant. The cotyledons of the *Cosmos bipinnatus* plant may then be cut and isolated as explants. According to an implementation, the temperature of the growth chamber can be in a range of, for example, about 20 to about 25° C. In another implementation, the predetermined photoperiods may be, for example, 16 hours in light and 8 hours in dark. According to another implementation, the seeds may be incubated in the growth chamber for a period of, for example, three days.

According to step 112, in order to prepare *Agrobacterium tumefaciens*, the *Agrobacterium tumefaciens* can first be cultured in a Lysogeny broth (LB) medium containing selective antibiotics. To this end, *Agrobacterium tumefaciens* that contain a R-glucuronidase (GUS) reporter gene (uidA) and a neomycin phosphotransferase gene (nptII), may be cultured overnight in a shaker incubator in an LB medium containing selective antibiotics, such as kanamycin (Kanamycin sulfate, Sigma-Aldrich, St. Louis, Mo. USA) and rifampicin (Rifampicin, Sigma-Aldrich, St. Louis, Mo. USA). In an aspect, the neomycin phosphotransferase gene (nptII) may be used for distinguishing transgenic plants, once transformed *Cosmos bipinnatus* plants are obtained.

According to an implementation, the temperature of the shaker incubator may be in a range of, for example, 25 to 29° C. and the rotor speed of the shaker incubator may be in a range of, for example, about 150 to about 200 RPM. In an implementation, the amount of selective antibiotics may be in a range of, for example, about 25 to about 100 mg/l.

After culturing *Agrobacterium* in the LB medium containing selective antibiotic, as was described hereinabove, the Agrobacteria may be pelleted in a centrifuge at a speed between, for example, about 3000 and about 5000 RPM for about 10 to about 30 minutes. The temperature of centrifuge may be set, for example, at about 4 to about 10° C.

Finally, the pelleted Agrobacteria may be suspended in an inoculation medium and diluted to a nal density, for example, of $OD_{600}$=0.8 in order to obtain an Agrobacteria suspension. The inoculation medium may be prepared using basal medium having, for example, 50-200 μM of a virulence gene stimulator; 10-20 mM of a pH regulator; 30-90 g/l of a carbon source; 0.5-8 mg/l of cytokinin; 0.5-8 mg/l of an ethylene action inhibitor; and 10-100 mg/l of a nitrogen source. In an implementation, the basal medium may be, for example, an MS medium. The virulence gene stimulator may be, for example, Acetosyringone (3,5-dimethoxy-4-hydroxyacetophenone). The pH regulator may be, for example, MES (4-Morpholineethanesulfonic acid). The carbon source may be selected from, for example, sucrose, maltose or glucose. The cytokinin may be, for example, benzyl adenine (BA) or Thidiazuron (TDZ). The ethylene action inhibitor may be, for example, silver nitrate. The nitrogen source may be selected from, for example, adenine sulfate or glutamine sulfate.

Moving on to step 113, in order to inoculate the explants that are obtained from step 111 with Agrobacteria that are prepared in step 112, the explants may be added to the Agrobacteria suspension. To this end, cotyledons explants of *Cosmos bipinnatus* may be soaked in, for example, 20-60 ml of the bacterial suspension for a duration, for example, about 1 to about 5 min and then they may be dried using, for example, a sterile filter paper in order to obtain inoculated explants.

Moving on to step 114, the inoculated explants are co-cultured with the prepared *Agrobacterium tumefaciens* in order to obtain transformed explants. To this end, the inoculated explants may be cultured for a duration, for example, of about 36 to about 72 hours in a co-cultivation medium; then they may be kept in the dark, at a temperature, for example, between 20 to 25° C. in a growth chamber. After co-cultivation, the explants may be washed, for example, with sterilized distilled water containing, for example, about 200-300 mg/l of an antibiotic that can be, for example, Cefotaxime.

Moving on to step 115, the co-cultured explants may be cultured in a regeneration medium for a period of about 5 to about 20 days in order to obtain regenerated shoots. The regeneration medium may contain a basal medium having, for example, about 2-5 mg/l of cytokinin, about 2-5 mg/l of an ethylene action inhibitor, and about 10-40 mg/l of a nitrogen source, and about 200-300 mg/l of antibiotics for eliminating the Agrobacteria. The basal medium can be, for example, MS medium. The cytokinin can be, for example, benzyl adenine (BA) or Thidiazuron (TDZ). The ethylene action inhibitor can be, for example, silver nitrate. The nitrogen source can be, for example, adenine sulfate or glutamine sulfate. The antibiotic can be, for example, Cefotaxime. After that, the co-cultured explants may be cultured in the same regeneration medium lacking antibiotics for a period of about 1 to about 3 months while they are subcultured by transferring some or all explants from a previous culture to a fresh growth medium every 2 weeks and eventually shoot induction will be observed on explants after 2 weeks of culture.

In an aspect, the regenerated shoots may be transferred to a selective medium for distinguishing transgenic plantlets among regenerated shoots. In an implementation, the selective medium may contain MS medium supplemented with, for example, about 200-300 mg/l of kanamycin as a selective antibiotic for a duration, for example, of about 0.5 to 2 months. The transgenic plantlets (i.e., transformed plantlets) are kanamycin resistant plantlets because they have a plasmid pBI121 containing neomycin phosphotransferase gene (nptII) as a kanamycin resistant gene due to the transformation with *agrobacterium*. Therefore, in the selective medium in the presence of kanamycin, only transgenic plantlets survive.

Moving on to step 116, the regenerated transformed shoots may be cultured in an elongation medium to obtain elongated transformed shoots. In an implementation, the elongation medium may contain an MS medium with, for example, about 0.5-3 mg/l of cytokinin. The cytokinin can be, for example, a BA hormone.

Moving on to step 117, the elongated transformed shoots or transgenic plantlets may be preserved in a rooting medium until rooted plantlets are formed. The rooting medium may contain an MS medium supplemented with, for example, about 0.05 to about 3 mg/l Indole-3-butyric acid (IBA). Once transformed *Cosmos bipinnatus* rooted plantlets are obtained they may either be transferred to a plant growth medium or be planted in a pot for further growth and flowering.

EXAMPLES

Example 1: Evaluating the Effect of BA, Silver Nitrate and Adenine Sulfate on Regeneration Frequency and Regenerated Shoot Number of Cotyledon Explants of *Cosmos bipinnatus*

In this example, direct regeneration of *Cosmos bipinnatus* plantlets was carried out with the following steps according to one or more aspects of the present disclosure. First, *Cosmos bipinnatus* seeds were sterilized. The sterilization of *Cosmos bipinnatus* seeds was carried out by soaking the seeds in an ethanol solution with a concentration of about 70% volume/volume for about 1 min followed by soaking the seeds in a hypochlorite sodium solution with a concentration of about 2% weight/volume for about 10 min, and then the seeds were rinsed three times with sterile distilled water.

The sterilized *Cosmos bipinnatus* seeds were then germinated in order to obtain cotyledons of *Cosmos bipinnatus* plant. Seed germination was carried out by putting the sterilized *Cosmos bipinnatus* seeds under a sterile condition in an agar-solidified MS medium. Then, the sterilized *Cosmos bipinnatus* seeds in the agar-solidified MS medium were incubated in a growth chamber with photoperiods of 16 hours in light and 8 hours in dark under fluorescent illuminations (60 µmol m² s¹) at 22° C.±1° C. for a period of 3 days. The cotyledons of *Cosmos bipinnatus* plant that grew from germinated seeds after 3 days were cut and used as explants in the following steps of the direct regeneration process.

Figure 2A:
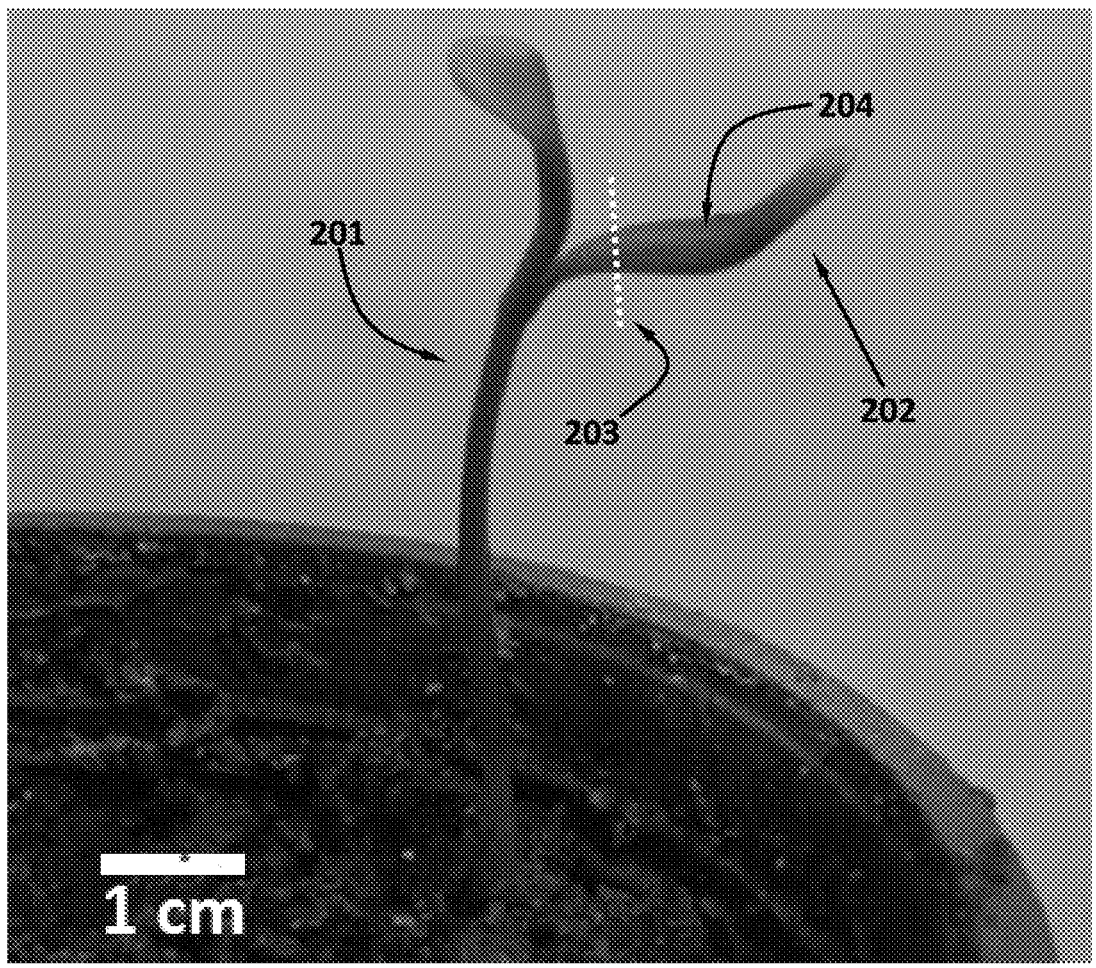
FIG. 2A illustrates a *Cosmos bipinnatus* plant.
Figure 2B:
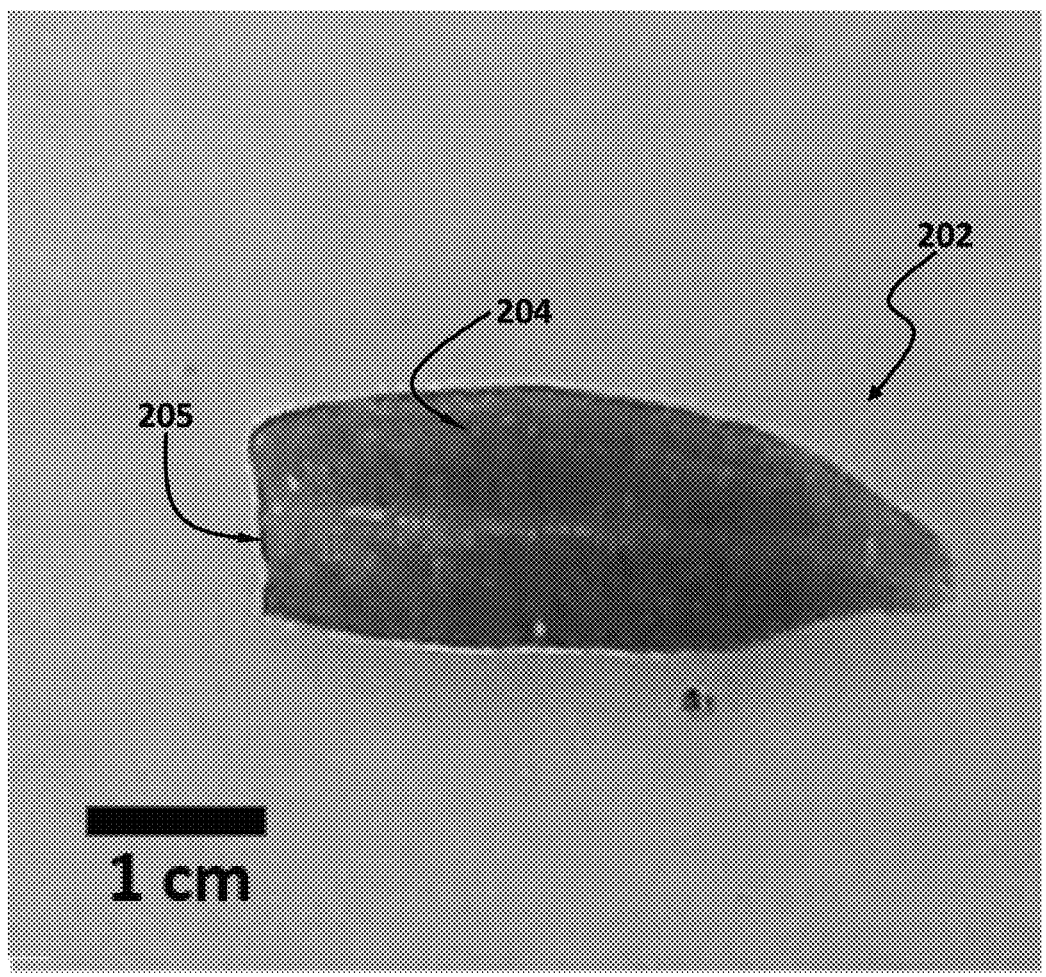
FIG. 2B illustrates a three-day old *Cosmos bipinnatus* cotyledon cut as an explant, as described in detail in connection with example 1.

FIG. 2A illustrates the cotyledon 202 of *Cosmos bipinnatus* plant that was be cut, along dotted line 203, from the *Cosmos bipinnatus* plant 201 that grew from germinated seeds after 3 days. FIG. 2B shows the cut three-day-old cotyledon 202 having a cut end 205 and an adaxial side 204, which was used as the explant in the direct regeneration process of *Cosmos bipinnatus* plantlets.

The obtained explants were then cultured onto a regeneration medium for regenerating cotyledon explants of *Cosmos bipinnatus*. To this end, 10 explants, with their adaxial side down, were cultured onto the regeneration medium in a Petri dish for regeneration in cotyledons to occur. The regeneration in cotyledons was assessed by examining shoot-inducing ability in the presence of different regeneration medium compositions. The different regeneration medium compositions included respectively different concentrations of plant growth regulators and ethylene inhibitors. The regeneration media contained benzyl adenine (BA), silver nitrate, and adenine sulfate with different concentrations. An MS medium supplemented with 3% sucrose was used as a basal medium and the pH was adjusted to about 5.8 using a 1 N solution of NaOH.

Table 1 reports the data on regeneration frequency of cotyledon explants of *Cosmos bipinnatus* in the presence of different regeneration medium compositions. As used herein, "regeneration frequency" is the percentage of the explants on which shoots initiated regeneration. A moderate percentage of regeneration (i.e., 50%) was obtained in the MS, supplemented with 5 mg/l BA+5 mg/l AgNO₃. In the media containing BA, adenine sulfate and AgNO₃, regeneration thrived significantly. In 5 mg/l BA+5 mg/l AgNO₃+ 20 mg/l adenine sulfate, the highest percentage of regeneration (i.e., 73.75%) was induced.

Figure 2C:
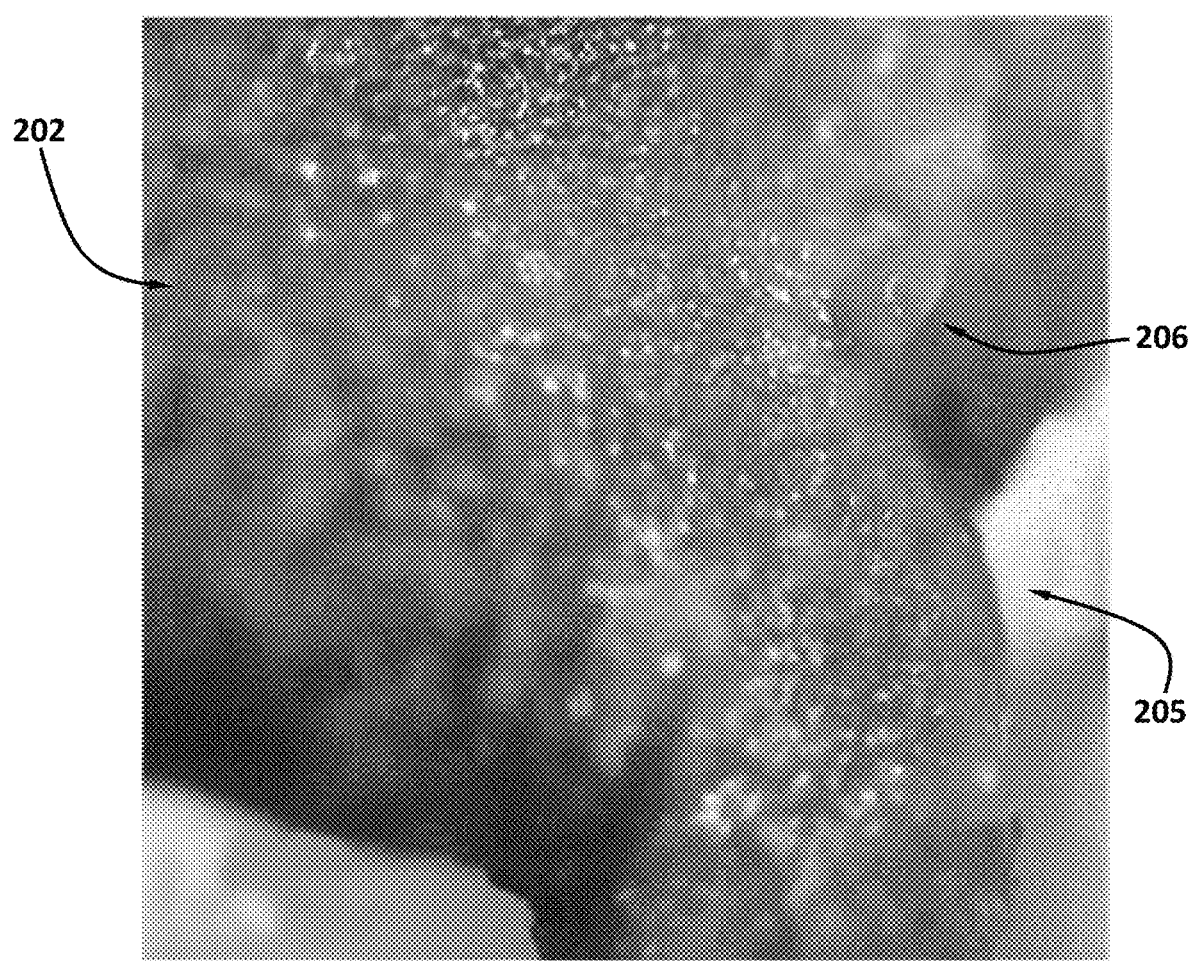
FIG. 2C illustrates a single regenerated shoot on a *Cosmos bipinnatus* explant.

FIG. 2C illustrates the initiation of regeneration on a cotyledon explant 202 in a shoot-inducing medium that contained 5 mg/l of BA, 5 mg/l of AgNO₃ and 20 mg/l of adenine sulfate. Referring to FIG. 2C, a single regenerated shoot 206 appears at the cut end 205 of the cotyledon explant 202.

Figure 2D:
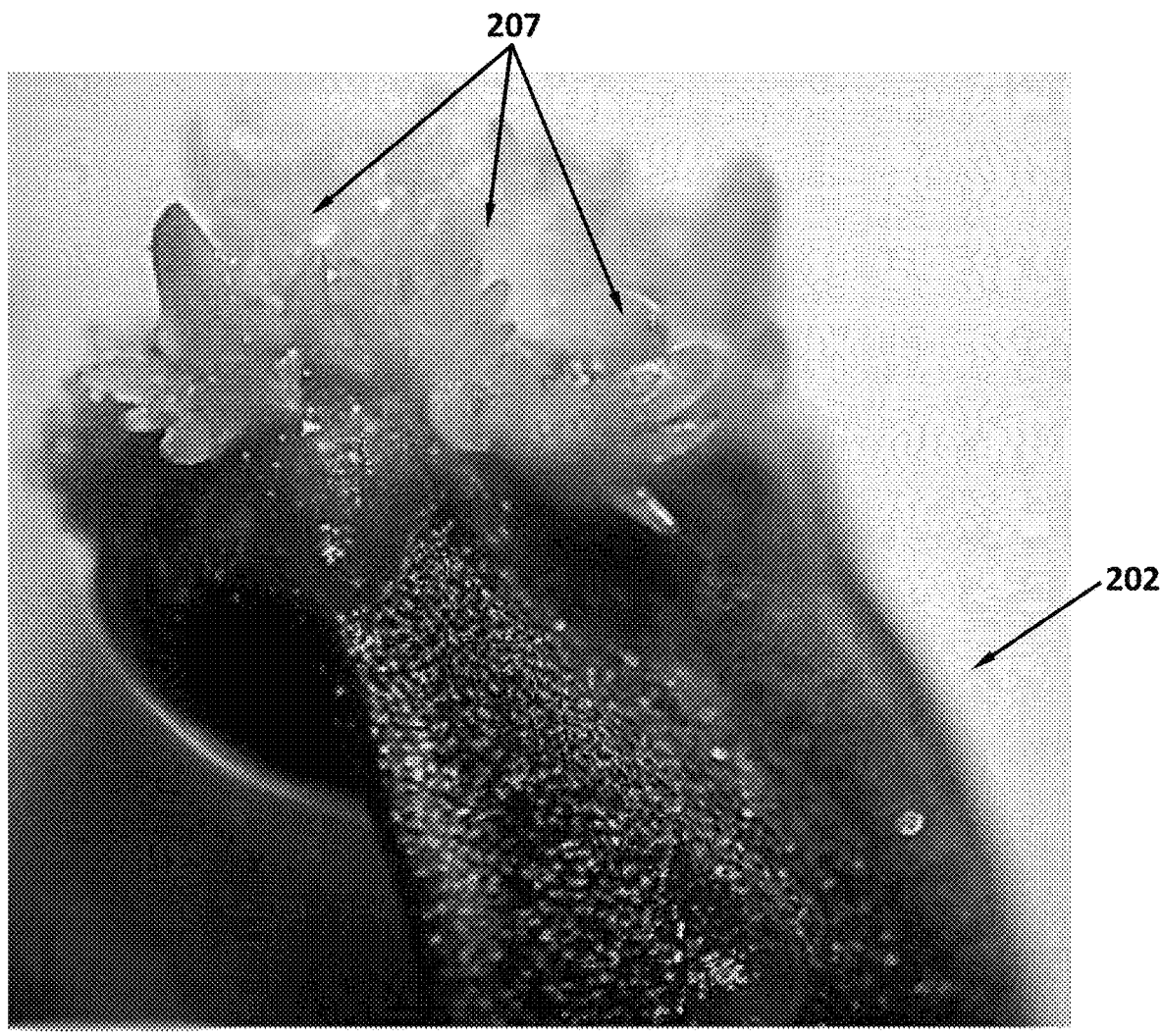
FIG. 2D illustrates a number of regenerated shoots on a *Cosmos bipinnatus* explant.

FIG. 2D illustrates the initiation of regeneration on a cotyledon explant 202 in a different shoot-inducing medium that contained 5 mg/l of BA, 5 mg/l of AgNO₃ and 40 mg/l of adenine sulfate. Referring to FIG. 2D, a number of regenerated shoots 207 appear at the cut end of the cotyledon explant 202.

The regenerated shoots from the explants, obtained as described above, were excised and transferred to a shoot elongation medium that contained a BA and an MS medium until the shoots were capable of being cultured onto a rooting medium, which will be described in detail in connection with example 2.

Figure 2E:
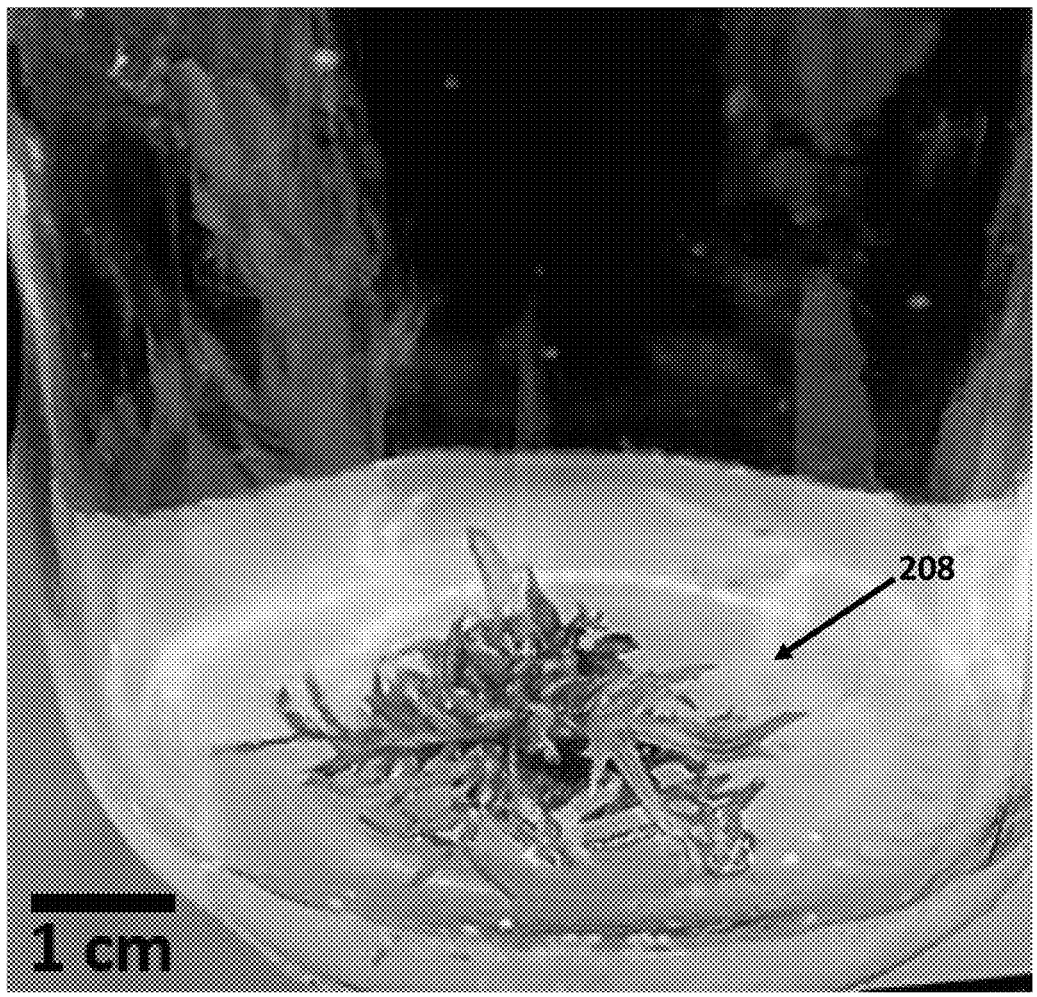
FIG. 2E illustrates regenerated shoots transferred onto an elongation medium, as described in detail in connection with example 1.
Figure 2F:
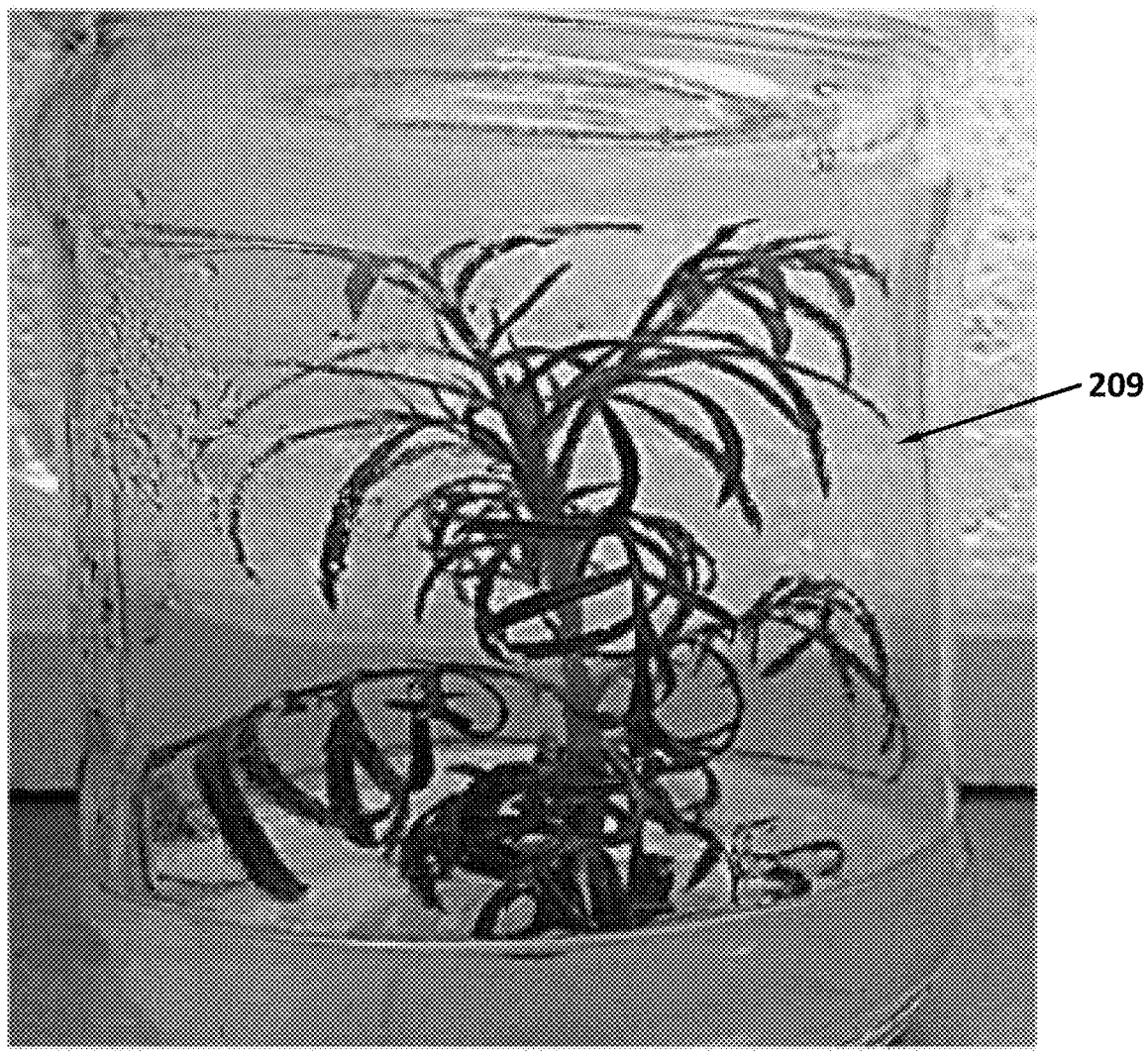
FIG. 2F illustrates elongated shoots, as described in connection with example 1.

FIG. 2E illustrates regenerated shoots 208 that were transferred onto an MS medium with 1 mg/l BA as the shoot elongation medium. FIG. 2F illustrates an elongated shoot 209 ready to be cultured onto a rooting medium.

TABLE 1

Regeneration frequency of cotyledon explants of *Cosmos Bipinnatus* in the presence of different regeneration medium compositions

| BA (mg/l) | AgNO₃ (mg/l) | Adenine sulfate (mg/l) | | | | |
|---|---|---|---|---|---|---|
| | | 0 | 10 | 20 | 40 | 80 |
| 0 | 0 | 0.001 ± 0.00 | 0.001 ± 0.00 | 0.001 ± 0.00 | 0.001 ± 0.00 | 0.001 ± 0.00 |
| 0 | 2.5 | 0.001 ± 0.00 | 12.50 ± 2.08 | 31.25 ± 5.37 | 25.00 ± 3.55 | 18.75 ± 3.94 |
| 0 | 5 | 0.001 ± 0.00 | 18.75 ± 4.85 | 31.25 ± 5.18 | 31.25 ± 4.78 | 25.00 ± 4.96 |
| 0 | 7.5 | 0.001 ± 0.00 | 12.50 ±4.20 | 12.50 ± 2.64 | 12.50 ± 2.08 | 6.25 ± 2.06 |
| 2.5 | 0 | 6.25 ± 0.00 | 18.75 ± 2.98 | 18.75 ± 4.78 | 25.00 ± 5.09 | 6.25 ± 2.50 |
| 2.5 | 2.5 | 38.75 ± 4.78 | 37.50 ± 6.45 | 43.75 ± 6.29 | 31.25 ± 4.78 | 31.25 ± 3.75 |
| 2.5 | 5 | 43.75 ± 4.78 | 50.00 ± 1.63 | 56.25 ± 6.29 | 50.00 ± 4.08 | 37.50 ± 6.45 |
| 2.5 | 7.5 | 17.75 ± 3.86 | 31.25 ± 4.78 | 31.25 ± 2.5 | 25.00 ± 5.77 | 12.50 ± 2.88 |

TABLE 1-continued

Regeneration frequency of cotyledon explants of *Cosmos Bipinnatus* in the presence of different regeneration medium compositions

| BA (mg/l) | AgNO$_3$ (mg/l) | Adenine sulfate (mg/l) | | | | |
|---|---|---|---|---|---|---|
| | | 0 | 10 | 20 | 40 | 80 |
| 5 | 0 | 6.25 ± 1.70 | 12.50 ± 2.88 | 31.25 ± 4.78 | 25.00 ± 4.08 | 12.50 ± 2.08 |
| 5 | 2.5 | 43.75 ± 4.78 | 50.00 ± 5.40 | 56.25 ± 3.09 | 50.00 ± 4.08 | 43.75 ± 4.78 |
| 5 | 5 | 50.00 ± 4.08 | 68.75 ± 6.29 | 73.75 ± 4.78 | 62.50 ± 2.88 | 56.25 ± 1.70 |
| 5 | 7.5 | 37.50 ± 6.45 | 43.75 ± 6.29 | 43.75 ± 4.78 | 31.25 ± 4.34 | 31.25 ± 2.98 |
| 7.5 | 0 | 5.25 ± 2.06 | 17.75 ± 5.61 | 25.00 ± 4.08 | 12.50 ± 2.88 | 12.50 ± 2.08 |
| 7.5 | 2.5 | 25.00 ± 0.00 | 37.5 ± 2.88 | 43.75 ± 3.40 | 31.25 ± 1.89 | 31.25 ± 1.50 |
| 7.5 | 5 | 37.50 ± 2.88 | 43.75 ± 3.30 | 43.75 ± 6.23 | 31.25 ± 2.06 | 25.00 ± 3.55 |
| 7.5 | 7.5 | 18.75 ± 6.49 | 17.75 ± 6.60 | 25.00 ± 1.63 | 11.25 ± 2.21 | 11.25 ± 1.70 |

Table 2 reports the data on shoot number of regenerated cotyledon explants of *Cosmos bipinnatus* in the presence of different regeneration medium compositions. As used herein, "shoot number" is the average number of shoots that are generated on the 10 explants used in the experiments for three replications. An average shoot number (i.e., 3.33) was obtained in an MS medium supplemented with 5 mg/l BA+5 mg/l AgNO$_3$ as the regeneration medium. In addition, a maximum shoot number per explants (i.e., 5.67) was observed on an MS medium supplemented with 5 mg/l BA, 5 mg/l AgNO$_3$ and 40 mg/l adenine sulfate as the regeneration medium.

TABLE 2

Shoot number of regenerated cotyledon explants of *Cosmos Bipinnatus* in the presence of different regeneration medium compositions.

| BA (mg/l) | AgNO$_3$ (mg/l) | Adenine sulfate (mg/l) | | | | |
|---|---|---|---|---|---|---|
| | | 0 | 10 | 20 | 40 | 80 |
| 0 | 0 | 0.00 ± 0.00 | 0.00 ± 0.00 | 0.00 ± 0.00 | 0.00 ± 0.00 | 0.00 ± 0.00 |
| 0 | 2.5 | 0.00 ± 0.00 | 0.34 ± 0.28 | 0.67 ± 0.22 | 1.00 ± 0.00 | 0.34 ± 0.28 |
| 0 | 5 | 0.00 ± 0.00 | 0.67 ± 0.05 | 1.34 ± 0.44 | 2.00 ± 0.23 | 0.67 ± 0.17 |
| 0 | 7.5 | 0.00 ± 0.00 | 0.67 ± 0.24 | 1.00 ± 0.00 | 1.34 ± 0.52 | 0.67 ± 0.08 |
| 2.5 | 0 | 1.34 ± 0.33 | 0.67 ± 0.20 | 2.34 ± 0.67 | 3.00 ± 0.58 | 1.34 ± 0.44 |
| 2.5 | 2.5 | 3.00 ± 0.46 | 4.00 ± 0.41 | 4.67 ± 0.16 | 4.67 ± 0.27 | 4.33 ± 0.17 |
| 2.5 | 5 | 2.34 ± 0.24 | 4.00 ± 0.50 | 4.62 ± 0.44 | 4.67 ± 0.33 | 3.33 ± 0.16 |
| 2.5 | 7.5 | 2.00 ± 0.25 | 2.26 ± 0.67 | 3.33 ± 0.20 | 3.67 ± 0.08 | 2.67 ± 0.16 |
| 5 | 0 | 0.34 ± 0.28 | 0.67 ± 0.16 | 1.67 ± 0.67 | 2.00 ± 0.42 | 1.00 ± 0.25 |
| 5 | 2.5 | 1.67 ± 0.67 | 3.67 ± 0.33 | 4.33 ± 0.13 | 4.67 ± 0.48 | 3.33 ± 0.16 |
| 5 | 5 | 3.33 ± 0.00 | 4.33 ± 0.08 | 4.33 ± 0.18 | 5.67 ± 0.44 | 3.67 ± 0.24 |
| 5 | 7.5 | 1.00 ± 0.25 | 2.67 ± 0.44 | 3.00 ± 0.36 | 3.33 ± 0.21 | 2.33 ± 0.33 |
| 7.5 | 0 | 0.67 ± 0.33 | 1.34 ± 0.20 | 1.67 ± 0.67 | 1.34 ± 0.17 | 0.67 ± 0.16 |
| 7.5 | 2.5 | 0.67 ± 0.22 | 2.00 ± 0.29 | 2.67 ± 0.44 | 2.33 ± 0.33 | 1.67 ± 0.16 |
| 7.5 | 5 | 0.67 ± 0.17 | 1.33 ± 0.44 | 1.67 ± 0.17 | 2.67 ± 0.08 | 1.33 ± 0.33 |
| 7.5 | 7.5 | 1.00 ± 0.23 | 1.33 ± 0.08 | 2.26 ± 0.55 | 1.67 ± 0.28 | 1.33 ± 0.16 |

Example 2: Evaluating Root Formation Frequency on Regenerated Plantlets of *Cosmos bipinnatus*

In this example, root formation frequency on regenerated plantlets was investigated. Here, the elongated shoots obtained as described above in example 1 were cultured on a rooting medium. Different types of rooting medium were used, as described hereinabove in reference to step 105.

Figure 2G:
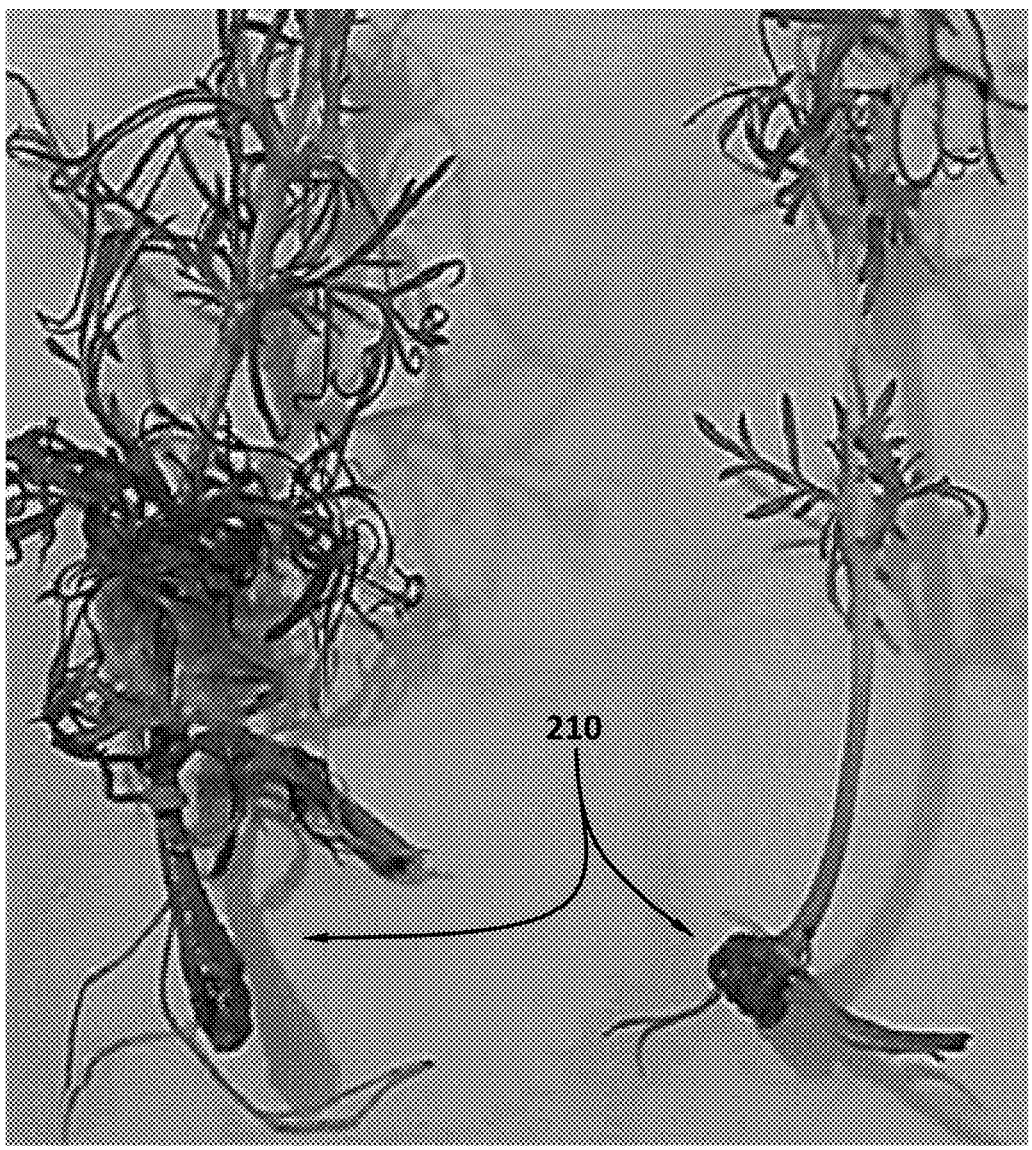
FIG. 2G illustrates *Cosmos bipinnatus* rooted plantlets, as described in detail in connection with example 2.

FIG. 2G illustrates root formation in regenerated *Cosmos bipinnatus* plantlets. Regenerated roots 210 are observed after a 3-week culturing period on the rooting medium.

After that, the rooted plantlets were washed and then some of the plantlets were transferred to a plant growth regulators-free MS medium, and other of the plantlets repetitions planted in pots containing peat moss and a perlite mixture with a ratio of 2:1 for a continued growth.

Figure 2H:
FIG. 2H illustrates flowered generate *Cosmos bipinnatus* plants.

FIG. 2H shows the plantlets producing flowers after being transferred to the plant regulators-free MS medium.

Example 3: Producing Transgenic Plantlets (Transformed Shoots) of *Cosmos bipinnatus*

In this example, transgenic plantlets of *Cosmos bipinnatus* cotyledons were produced by a method with the following steps. *Cosmos bipinnatus* cotyledons as explants were first prepared and isolated as described in example 1.

A disarmed *Agrobacterium Tumefaciens* strain LBA4404 harboring a binary vector pBI121, which contains a R-glucuronidase (GUS) reporter gene (uidA) and a neomycin phosphotransferase gene (nptII) for distinguishing transgenic plantlets was cultured overnight in a shaker incubator (170 rpm) at 28° C. in 50 ml of liquid LB medium (10 g/l tryptone peptone, 5 g/l Bacto™ yeast extract, 10 g/l NaCl, pH 7.0) containing selective antibiotics as described hereinabove in reference to step 112.

Agrobacteria were pelleted at 4000 rpm for 12 min in a 4° C. centrifuge, then re-suspended in an inoculation medium that contained an MS medium supplemented with 100 μM Acetosyringone (3,5-dimethoxy-4-hydroxyacetophenone; Sigma-Aldrich, St Louis, Mo., USA), 10 mM of MES (4-Morpholineethanesulfonic acid, Sigma Aldrich, St Louis, Mo., USA), 30 g/l of sucrose, 5 mg/l of BA+5 mg/l of silver nitrate and 20 mg/l of Adenine sulfate. The obtained bacterial suspension was diluted to a nal density of OD (wave length 600)=0.8.

The cotyledon explants of *Cosmos bipinnatus* were soaked in 30 ml of bacterial suspension for 1-5 min and then were dried on a sterile filter paper. After that they were cultured for 48 hours on a co-cultivation medium that contained an MS medium supplemented with 100 μM Acetosyringone (3,5-dimethoxy-4-hydroxyacetophenone; Sigma-Aldrich, St Louis, Mo., USA), 10 mM of MES (4-Morpholineethanesulfonic acid, Sigma Aldrich, St Louis, Mo., USA), 30 g/l of sucrose, and 5 mg/l of BA+5 mg/l of silver nitrate and 20 mg/l of Adenine sulfate+agarose while they were kept in the dark, at a temperature of about 22° C.±2 in the growth chamber. After co-cultivation, the explants were washed with sterilized distilled water containing 200 mg/l cefotaxime (Cefotaxime sodium salt, Sigma Aldrich, St. Louis, Mo. U.S.A.)

The explants were then cultured on a regeneration medium containing 5 mg/l BA+5 mg/l Silver nitrate+20 mg/l Adenine sulfate for a period of 10 days. The regeneration medium was supplemented with 200 mg/l cefotaxime for elimination of *Agrobacterium*.

The explants were then cultured onto the same regeneration medium lacking antibiotics for a period of 2 months and then sub-cultured every 2 weeks. Shoot induction was observed on explants after 2 weeks of culture.

Shoots from the cotyledon explants were excised and maintained in a shoot elongation medium containing 1 mg/l BA and MS medium until the shoots were capable of being cultured on a rooting medium.

Transgenic plantlets were distinguished from among non-transgenic plants on an MS medium supplemented with 75 mg/l kanamycin. Kanamycin functions as a selectable marker. Non-transgenic plants were sensitive to kanamycin and they turned white, while transgenic plants were resistant to kanamycin and remained green and strong.

Figure 3A:
FIG. 3A shows a non-transgenic plant in an MS medium containing kanamycin as the marker, described in detail in connection with example 3.
Figure 3B:
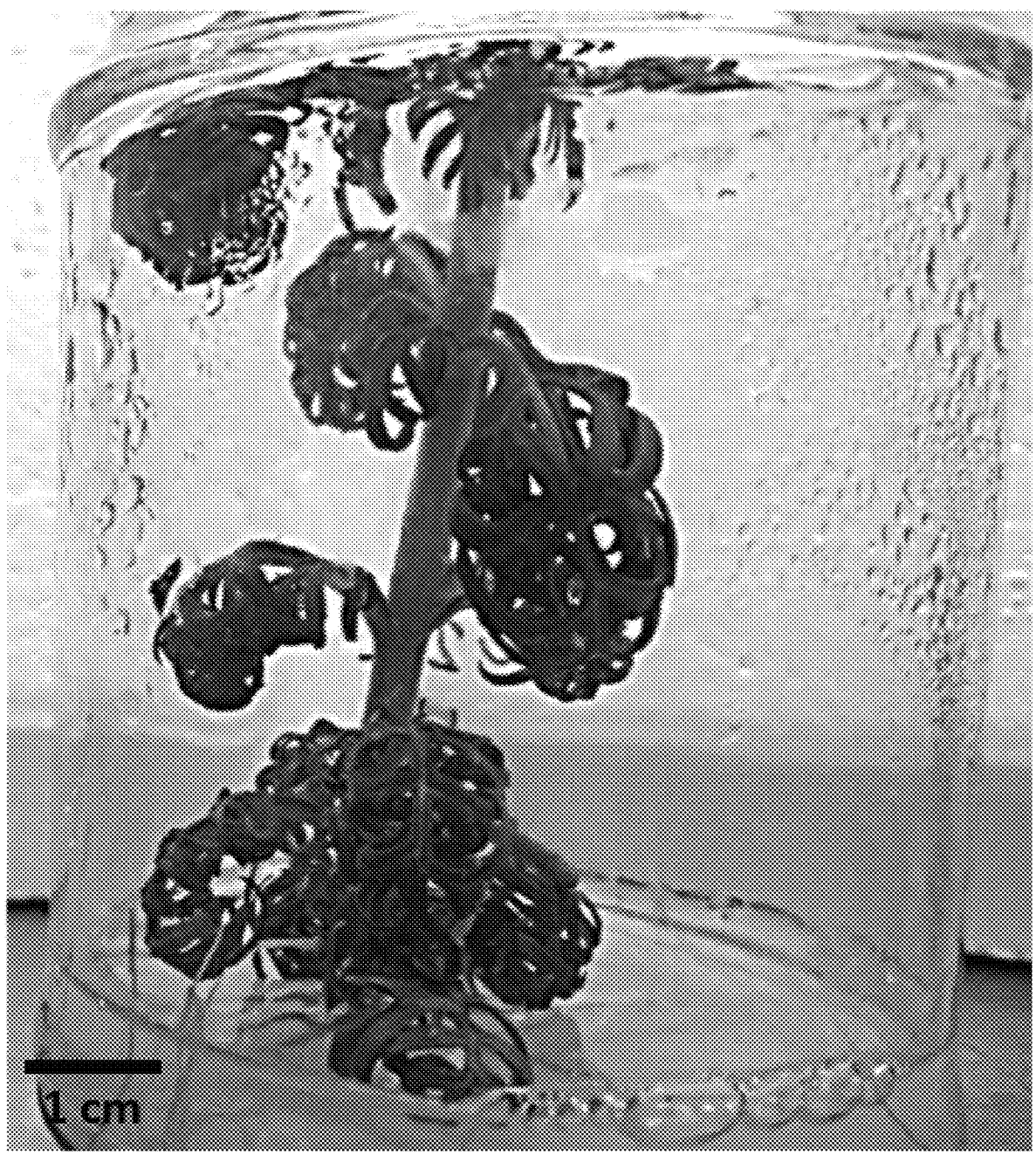
FIG. 3B shows a transgenic plant in an MS medium containing kanamycin as the marker, described in detail in connection with example 3.

FIG. 3A shows a non-transgenic plant in an MS medium containing kanamycin as the marker. The non-transgenic plant turned white due to its sensitivity to kanamycin. FIG. 3B shows a transgenic plant in an MS medium containing kanamycin as the marker. The transgenic plant remained green and strong.

The transgenic shoots were preserved on a rooting medium until rooted plantlets were organized; after washing the rooted plantlets, the transgenic plantlets were transferred for continued growth.

Example 4: GUS Assay for Determining Transformation Efficacy

In this example, histochemical β-glucuronidase (GUS) assay was carried out to measure the transient GUS gene expression. Since 5-bromo-4-chloro-3-indolyl glucuronide (X-Gluc) can detect the β-glucuronidase (GUS) enzyme activity in tissues and cells, it was used as a substrate in the GUS assay. First, 0.1 g of the regenerated transformed plantlets, obtained as described in connection with Example 3, were subjected to transient histochemical GUS assay; to this end, tissue samples were incubated in a 2 ml tube containing GUS histochemical staining buffer for 72 hour at 37° C. while the tube was wrapped in aluminum foil. GUS histochemical staining buffer contains sodium phosphate buffer, Triton X100, Ferro-cyanide, ferri-cyanide, X-Gluc, H2O. The details of these stock solutions and their concentrations are presented in Table 4. After that, the tissues were bleached overnight with an ethanol solution with a concentration of about 70% volume/volume. β-glucuronidase enzyme is able to cleave the chromogenic substrate X-Gluc, and it causes an insoluble blue color to be produced in those plant cells that demonstrate GUS activity. The transformation efficiency of plantlets was evaluated by observing the insoluble blue color, which is an indicator of GUS enzyme activity on each of the transgenic plantlets.

Figure 4A:
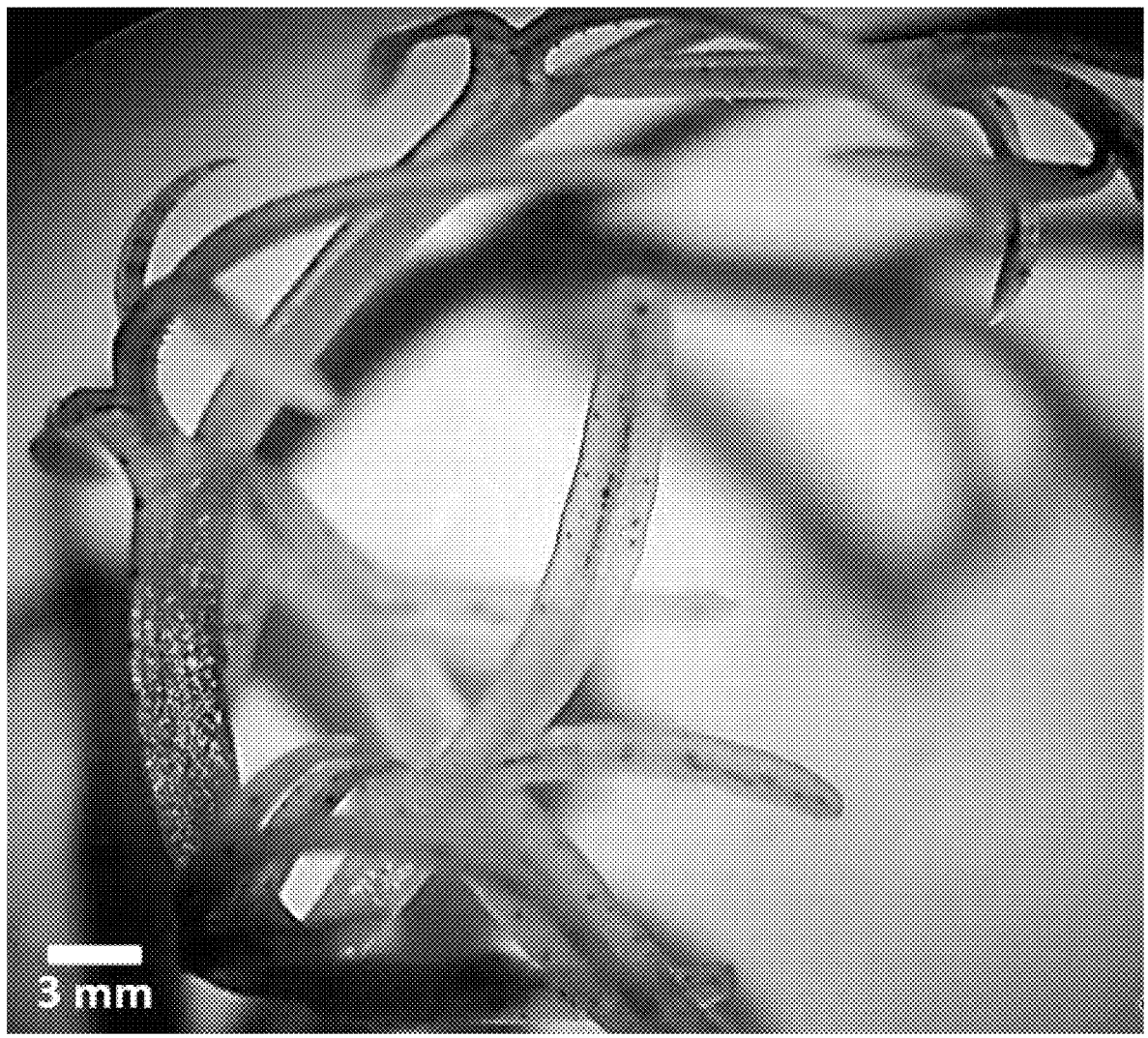
FIG. 4A shows a non-transgenic plant subjected to transient histochemical GUS assay, as described in detail in connection with example 4.
Figure 4B:
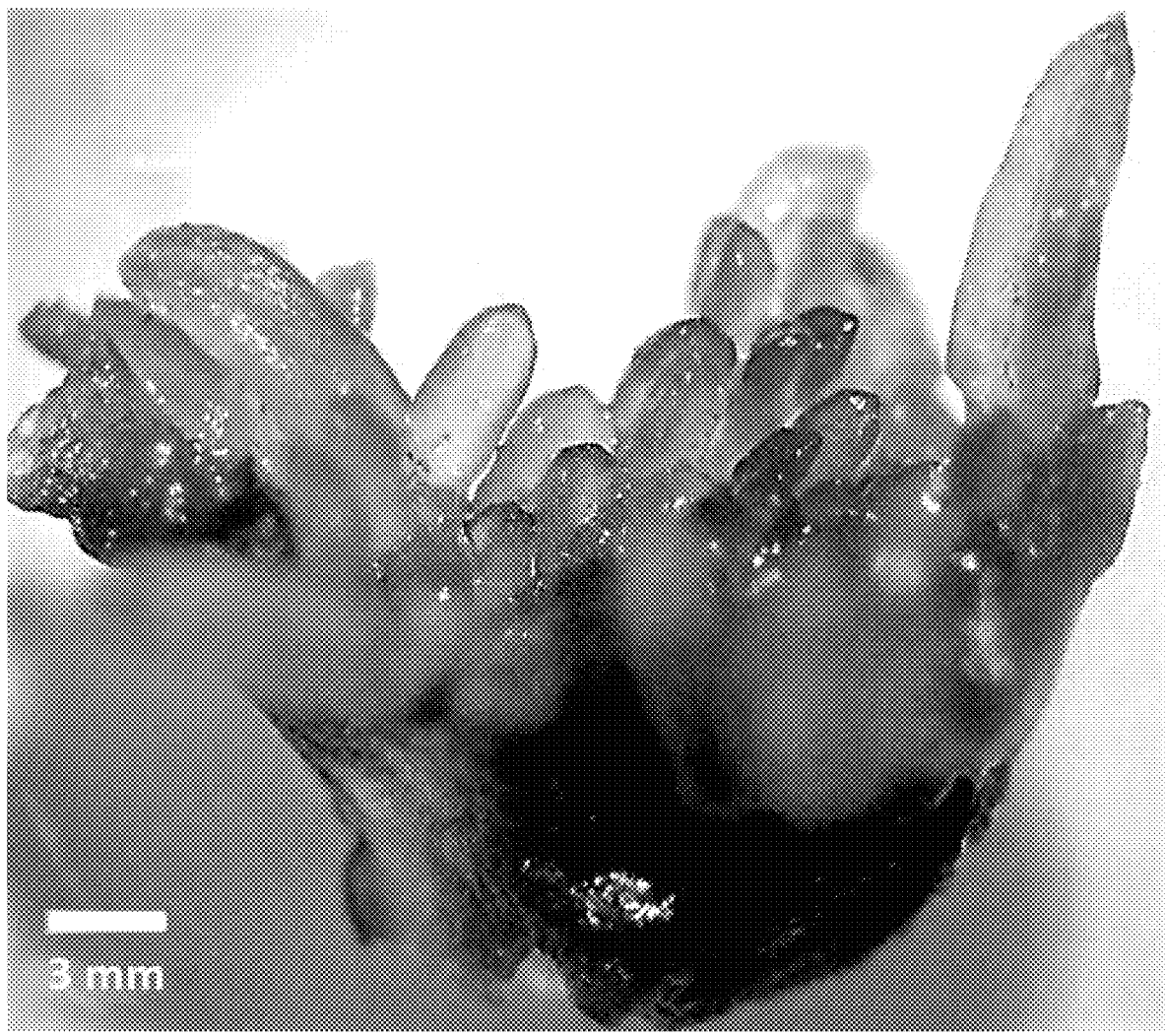
FIG. 4B shows a transgenic plant subjected to transient histochemical GUS assay, as described in detail in connection with example 4.

FIG. 4A shows a non-transgenic plant, which turned to white. As seen in FIG. 4B transgenic plants demonstrated GUS expression and turned to blue, which is visible as a dark color in this figure.

TABLE 4

| Stock solution | Final concentration | GUS stain (50 ml) |
|---|---|---|
| 1M Sodium phosphate buffer pH: 7 | 50 mM | 2 ml |
| 10% Triton X100 | 0.2% | 1 ml |
| 0.1M Ferro-cyanide | 5 mM | 2.5 ml |
| 0.1M Ferri-cyanide | 5 mM | 2.5 ml |
| $H_2O$ | — | 40.44 ml |
| 100 mM X-Gluc | 2 mM | 1 ml |

Example 5: Evaluating Effect of MS Medium on Percentage of Transgenic Plantlets of *Cosmos bipinnatus*

In this example, the effect of the MS medium on the percentage of transgenic plantlets of *Cosmos bipinnatus* was investigated using different inoculation and co-cultivation media in the process of regenerating transformed *Cosmos bipinnatus* cotyledons, which was described in connection with example 3. Three different inoculation and co-cultivation media were used and their compositions are reported in Table 5.

The experiments were designed based on a completely randomized design with three replications using SAS statistical analysis package (SAS Inc. Cary, USA) with three Petri dishes for each experiment, and with 15 explants in each Petri dish.

Table 6 reports the results of experiments on the effect of different MS media, co-cultivation conditions, and inoculation time on the percentage of transgenic plantlets of *Cosmos bipinnatus* among all regenerated plantlets. The percentage of transgenic plantlets is represented by the percentage of kanamycin-resistant plantlets of *Cosmos bipinnatus* among all regenerated plantlets. The highest percentage of kanamycin-resistant plantlets (i.e., 13.30%) was observed in the experiment carried out with medium 2 (MS-(KH2PO4, NH4NO3, KNO3, and CaCl2)).

TABLE 5

| Name of Medium | Inoculation and Co-cultivation Medium |
|---|---|
| Medium 1 | Full MS |
| Medium 2 | MS - ($KH_2PO_4$, $NH_4NO_3$, $KNO_3$, $CaCl_2$) |
| Medium 3 | MS - ($KH_2PO_4$, $NH_4NO_3$, $KNO_3$, $CaCl_2$, $MgSO_4$, micro elements, $Na_2EDTA$, $FeSO_4$, Vitamins) . . . only distilled water, sucrose, Agar |

TABLE 6

| Medium | Co-cultivation condition | Inoculation time | Frequency of Transformation % (Mean ± SE) |
|---|---|---|---|
| Medium 1 | Day | 1 min | 4.90 ± 0.75 |
| Medium 1 | Day | 5 min | 6.67 ± 0.43 |
| Medium 1 | Night | 1 min | 3.40 ± 0.22 |
| Medium 1 | Night | 5 min | 5.18 ± 0.47 |
| Medium 2 | Day | 1 min | 8.34 ± 0.31 |
| Medium 2 | Day | 5 min | 13.30 ± 0.87 |
| Medium 2 | Night | 1 min | 7.30 ± 0.76 |
| Medium 2 | Night | 5 min | 10.00 ± 0.65 |
| Medium 3 | Day | 1 min | 8.67 ± 0.46 |
| Medium 3 | Day | 5 min | 10.20 ± 0.38 |
| Medium 3 | Night | 1 min | 3.34 ± 0.21 |
| Medium 3 | Night | 5 min | 5.31 ± 0.40 |

What is claimed is:

1. A method for *Cosmos bipinnatus* plant transformation and regeneration, the method comprising:
    isolating *Cosmos bipinnatus* cotyledons as explants;
    preparing *Agrobacterium tumefaciens* as an Agrobacteria suspension;
    inoculating the explants with the prepared *Agrobacterium tumefaciens*;
    co-culturing the inoculated explants with the prepared *Agrobacterium tumefaciens* in a co-cultivation medium to obtain transformed explants; and
    culturing the transformed explants in a regeneration medium to obtain regenerated transformed shoots by placing the transformed explants in a dish containing the regeneration medium with adaxial side of the transformed explants down, wherein the regeneration medium includes a basal medium, Thidiazuron (TDZ), an ethylene action inhibitor, glutamine sulfate, and antibiotics for eliminating the *Agrobacterium*.

2. The method according to claim 1, wherein the basal medium is a Murashige and Skoog (MS) medium.

3. The method according to claim 1, wherein the TDZ has a concentration in a range of 2 mg/l to 5 mg/l.

4. The method according to claim 1, wherein the ethylene action inhibitor is silver nitrate.

5. The method according to claim 4, wherein silver nitrate has a concentration in a range of 2 mg/l to 5 mg/l.

6. The method according to claim 1, wherein the ethylene action inhibitor has a concentration in a range of 2 mg/l to 5 mg/l.

7. The method according to claim 1, wherein the glutamine sulfate has a concentration in a range of 10 mg/l to 40 mg/l.

8. The method according to claim 1, wherein isolating the *Cosmos bipinnatus* cotyledon includes:
    sterilizing *Cosmos bipinnatus* seeds;
    germinating sterilized *Cosmos bipinnatus* seeds to obtain cotyledons of *Cosmos bipinnatus* plant; and
    cutting the cotyledons from the *Cosmos bipinnatus* plant, to obtain explants.

9. The method according to claim 1, wherein preparing the *Agrobacterium tumefaciens* includes:
    culturing the *Agrobacterium tumefaciens* in a Lysogeny broth (LB) containing selective antibiotics;
    inoculating the *Agrobacterium tumefaciens* in an inoculation medium to obtain an Agrobacteria suspension.

10. The method according to claim 1, wherein inoculating the explants with the prepared *Agrobacterium tumefaciens* includes soaking the explants in an agrobacteria suspension.

11. The method according to claim 1, wherein the antibiotics for eliminating the *Agrobacterium* include Cefotaxime.

12. The method according to claim 1, wherein the antibiotics for eliminating the *Agrobacterium* are present in the regeneration medium with a concentration of 200 to 300 mg/l.

13. The method according to claim 1, further comprising:
    culturing the regenerated transformed shoots onto an elongation medium to obtain elongated transformed shoots; and
    culturing the elongated transformed shoots onto a rooting medium to obtain rooted transformed *Cosmos bipinnatus* plantlets.

* * * * *